(12) United States Patent
Gravagna et al.

(10) Patent No.: US 6,605,066 B1
(45) Date of Patent: Aug. 12, 2003

(54) DEVICE FOR FORMING AND DELIVERING A MIXTURE

(75) Inventors: Philippe Gravagna, Irigny (FR); Jean-Louis Tayot, La Tour de Salvagny (FR)

(73) Assignee: Imedex Biomateriaux (FR)

( * ) Notice: Subject to any disclaimer, the term of this patent is extended or adjusted under 35 U.S.C. 154(b) by 0 days.

(21) Appl. No.: 09/554,577

(22) PCT Filed: Sep. 15, 1999

(86) PCT No.: PCT/FR99/02197

§ 371 (c)(1),
(2), (4) Date: Aug. 29, 2000

(87) PCT Pub. No.: WO00/16698

PCT Pub. Date: Mar. 30, 2000

(30) Foreign Application Priority Data

Sep. 18, 1998 (FR) .............................................. 98 11700

(51) Int. Cl.[7] .......................... A61M 5/00; A61M 5/178; A61M 37/00; A61M 31/00; A61L 9/04
(52) U.S. Cl. ......................... 604/191; 604/518; 604/82; 604/83; 604/186; 424/45

(58) Field of Search ............................. 604/82, 83, 191, 604/43, 130, 116, 164.11, 264, 35, 139; 606/210; 424/45

(56) References Cited

U.S. PATENT DOCUMENTS

| | | | | |
|---|---|---|---|---|
| 5,116,315 A | * | 5/1992 | Capozzi et al. | ............. 222/137 |
| 6,047,861 A | * | 4/2000 | Vidal et al. | ................. 222/137 |
| 6,099,514 A | * | 8/2000 | Sharkey et al. | ............. 604/264 |
| 6,537,246 B1 | * | 3/2003 | Unger et al. | ................. 604/82 |

* cited by examiner

*Primary Examiner*—Manuel Mendez
*Assistant Examiner*—Roz GhaFoorian
(74) *Attorney, Agent, or Firm*—Larson & Taylor, PLC

(57) ABSTRACT

A device for the formation and delivery of a mixture, notably a surgical adhesive, consisting of a receptacle adapted for easy handling by the surgeon, and including the means of receiving two syringe barrels containing the constituents of the mixture, the means of simultaneously expelling the contents, the means of maintaining the contents of syringe containing the first constituent, at a predetermined temperature setting which is higher than body temperature, and a mixer simultaneously receiving the contents of the two syringes, and the mixer also being used for cooling.

31 Claims, 7 Drawing Sheets

DEVICE FOR FORMING AND DELIVERING A MIXTURE

Device for the formation and delivery of a mixture, notably for the surgical application of this mixture.

The present invention concerns a device for the formation and application of a mixture of two constituents, notably, the delivery of a mixture for surgical application, such as, in particular, a collagen preparation.

Collagen preparations, designed for application in fluid form, as a liquid or paste, for example, have already been proposed for surgical application, notably in the form of surgical adhesive.

Application WO 97/29715 concerned the proposal of adhesives made from a mixture of gelatine and a polyaldehyde type of crosslinking agent, to produce a fluid mixture for application at a relatively high temperature, above 50° C. Such temperatures are much too high for some tissues, notably in central nervous system surgery, fine innervated, vascularized tissues such as vascular and digestive walls, particularly the blood vessels, heart, intestines and uterus. It should be emphasized that official standards require a temperature lower than 41° C. for the product applied.

Collagen preparations are also known in the form of adhesive described in application WO 98/15299, applied in the form of a mixture of a collagenic substance and a polyaldehyde agent, for example, starch. This mixture can be applied in fluid form at a temperature of around 37° C., which is optimal. This type of mixture is characterized particularly by a substance of collagenic origin as defined in the afore-mentioned application, for example, a collagen which has lost at least part of its spiral, non hydrolyzed structure, consisting mainly of alpha chains.

For these preparations, to make an extemporaneous mixture easily, i.e. prepared at the time the surgeon is ready to apply the preparation consisting of a collagenic substance and a crosslinking agent, it is favourable to raise the collagenic preparation to a temperature higher than the application temperature, for example to a temperature of around 42° C. to 50° C., necessary to achieve adequate fluidity. The problem is then to administer the mixture to the receiving tissue at a temperature close to body temperature at 37° C., or in any case, lower than 41° C.

It has already been proposed to make these mixtures at the last moment, having previously raised the temperature of the preparation of collagenic substance in a drying oven or a water bath. This method of preparation has a number of disadvantages, however, for use under hospital conditions, notably because the heated product begins to cool as soon as it leaves the thermostatically controlled atmosphere, so that the temperature of the product applied is not constant and is difficult to control.

The invention therefore proposes to provide a device which can be used to prepare an extemporaneous mixture, at the time of application by the surgeon, of a collagenic substance and a crosslinking agent, for delivery of a mixture at a temperature close to body temperature.

It should be noted that this objective is made particularly difficult in that collagen or gelatine solutions are extremely viscous, whereas solutions of crosslinking agents display very low viscosity and it is difficult to mix fluids of very different viscosities.

Another of the invention's objectives is to provide such a device which displays a high level of safety with respect to delivery at the required temperature.

Another of the invention's objectives is to provide such a device which can be used to provide several deliveries separated by time intervals likely to cause considerable polymerization of the mixture.

Another of the invention's objectives is to provide such a device which is extremely practical to use.

Another objective is to provide such a device which can be used to deliver the mixture in the form of a foam.

The invention's objective is to provide a device for the formation and delivery of a mixture, notably for the surgical application of this mixture, characterized in that it includes:

a receptacle suitably shaped for handling by the surgeon and including means of holding two syringe barrels, these being a syringe containing the first constituent of the mixture, for example, a collagenic solution, and a syringe containing the second constituent of the mixture, for example, a solution of crosslinking agent;

means for simultaneously expelling the contents of the two syringes;

the means of maintaining the contents of the syringe holding the first constituent, for example, the collagenic solution, at a fixed temperature in excess of body temperature, for example, about 45° C. to 50° C.

and a mixer receiving the contents of both syringes simultaneously during application, which mixing device also secures cooling.

The means of heating the contents of the syringe favourably includes an electrical resistance or thermistor. This resistance can be fitted to the receptacle itself.

It is preferable, however, that this electrical resistance should be permanently fastened to the barrel of the syringe, for example, in the form of a resistance embedded in a film glued around the body of the syringe. The electrical power supply for this film can be provided, for example, by conductors connected to the film and terminating in a means of connection to a source of electrical power, either directly from an appropriate battery, or by using a complementary means of connection which is then connected to the source of electrical power. In this last case, when the device is in use, the user must also connect the conductors leading from the barrel of the syringe to the complementary means of connection.

A thermostat can be used favourably, preferably also fixed to the barrel of the syringe, to control the power supply to the thermistor and detect when the required temperature is reached. This thermostat then preferably emits a signal, informing the surgeon that the syringe has reached the desired temperature. Setting and fitting such a thermostat are routine operations for technicians.

Preferably, an extra safety thermostat is provided in the circuit, this thermostat being designed to cut the thermistor's power supply when a temperature safety threshold is reached or exceeded, this thermostat, in addition, only restoring the power supply once the temperature has fallen back to a level which is substantially below the predetermined temperature setting, so that the first thermostat cannot emit a signal before a new correct heating cycle has been completed.

The mixer will preferably include a removable connector used to receive the contents of the two syringes and carry them to the inlet of an end-piece or mixer body extension containing a device fitted with baffles providing obstacles which gradually produce a homogeneous mixture.

This mixer body will preferably include extended particles and it is particularly preferred that these particles be formed of small sections of plastic tubing or other cut in two across the diameter. It was observed that this type of structure ensures intermingling of the particles leading to obtention of the mixture required, over a short distance of a few centimetres, while ensuring that the temperature falls during its passage through the mixer, which constitutes one of the invention's characteristics.

The connector and mixer end-piece can preferably be removed separately and are replaceable, which means that the contents of the syringes can be used in several successive applications, separated by long periods in spite of the start of polymerization of the mixture in the end-piece or body of the mixer which will simply be replaced.

In the preferred application of the invention, using a collagen constituent or gelatine, as defined, for example in WO 98/15299, the volume of the expellable contents of the syringe containing the first constituent, i.e. the collagenic constituent, is about three to ten times as much, for example four times as much as that of the contents of the second syringe, i.e. the solution of crosslinking agent, such as a solution of oxidized starch.

When the collagenic constituent of the first syringe is in the form of a homogeneous liquid solution, this ratio is preferably between 3 and 6. When the collagenic constituent of the first syringe is in the form of a liquid foam containing air in emulsion in an aqueous solution, this ratio must be increased to 6 to 10. Indeed, the second syringe must be smaller to take into account the reduced volume of aqueous solution in the first syringe.

Preferably, the conduit from the connector which is connected to the first syringe, is subdivided into several channels so that several equidistant feeds are produced leading into the mixer end-piece or body, while the conduit connected to the second syringe forms only a single central channel.

Thus, for example, the single channel is positioned centrally in the connector and the four equidistant channels connected to the first syringe are positioned concentrically around the singe channel.

The outlet of the four channels penetrates the start of the mixer end-piece where the mixture will be made homogeneously.

For application of such a collagenic mixture, it is preferable for the temperature of the contents of the first syringe, containing the original collagenic constituent, to be raised by the electrical heating system, to a constant temperature selected within the 42° C. to 57° C. range and: preferably between 44° C. and 50° C., the other constituent, i.e. the crosslinking agent being at ambient temperature, generally the temperature of the operating theatre; the length of the mixer end-piece is then preferably around 2 to 4 cm and it is observed that it is possible to obtain an extremely homogeneous mixture at the outlet, at a temperature of around 37° C., and below 41° C.; or preferably between 48° C. and 54° C., the other constituent being at ambient temperature, the length of the mixer end-piece being 2 to 4 cm and extended by a laparoscopy tube, preferably around 25 to 35 cm long.

The mixture which is delivered by this device according to the invention, can be a mixture which is delivered in the form of a liquid or a fluid gel, or in the form of a foam resulting from an emulsion using a preferably sterile gaseous constituent, for example, air.

The foam can be formed in situ in the mixer by discharging a source of gas into the mixer, for example at the inlet or during its passage through the mixer. This source of gas can be a third syringe containing the gas, the content of which is expelled at the same time as that of the other two syringes to pass through the mixer simultaneously.

Still considering the case of a mixture in the form of foam, the first constituent of the mixture can itself be a foam, which may either be formed in the barrel of the first syringe or introduced into this barrel, transported, if necessary, and maintained in this barrel at the predetermined temperature setting, which also keeps the foam stable.

The first foam constituent can be prepared either in the barrel of the syringe or outside it, for example in another syringe connected to the first one, by mixing the gas to the liquid constituent. As a variant, the foam can be prepared favourably by mixing a dry powder, consisting of the protein components of the first constituent, and a gas, for example, air, with the solvent, for example, physiological saline. Very favourably, the gas used can be the one which is naturally contained or incorporated in the empty volume of a powder form of the protein element in proportion to the swelling ratio of this powder, the solvent then being added to this biphasic solid-gas mixture.

These various variants of the formation of the first foam constituent can appropriately use the barrel of the first syringe, i.e. the syringe which is likely to be heated, and another syringe, each one containing one or more components of the constituent, which, when they are mixed, form the foam, preferably by successive repeated transfers from one syringe to the other, the foam formed being finally contained in the first syringe fitted with the heating means.

As a variant, instead of an extra syringe, the heating syringe can be connected to a flask of appropriate volume, such that injecting the contents of the syringe into the flask causes excess pressure which pushes the contents into the syringe when the plunger is released.

The invention also concerns a set, or kit consisting of a receptacle, as defined in the present invention, a first syringe barrel containing a first constituent, sealed by a stopper, a second syringe barrel containing the second constituent, sealed by a stopper, and a mixer end-piece containing the intermingled particles.

The first constituent is preferably a collagen solution as defined in application WO 98/15299, or an aqueous collagen foam in an emulsion with a gas, for example, air, and the second constituent is a polyaldehyde solution, notably oxidized starch.

The invention also concerns the processes used to prepare the liquid or foam-based mixtures described above.

The invention also concerns a syringe fitted with the means for maintaining its contents at a predetermined temperature setting, for example, close to body temperature, or higher, for example, around 45° C. to 50° C.

This syringe can be used in the device or kit described above, but it can also be used individually, its content being used in any other application.

Among these applications, one consists of heating the syringe containing a viscous product to reduce the viscosity and facilitate administration, for example, hyaluronic acid or gelatine or collagen, for example, for intra-ocular administration.

In another application it is used to heat a previously frozen product to accelerate and facilitate its use.

The means described above can be used to advantage as the means of maintaining the temperature.

Other advantages and characteristics of the invention will appear on reading the following description, provided as a non-limiting example and referring to the appended drawing in which.

Figure 1:
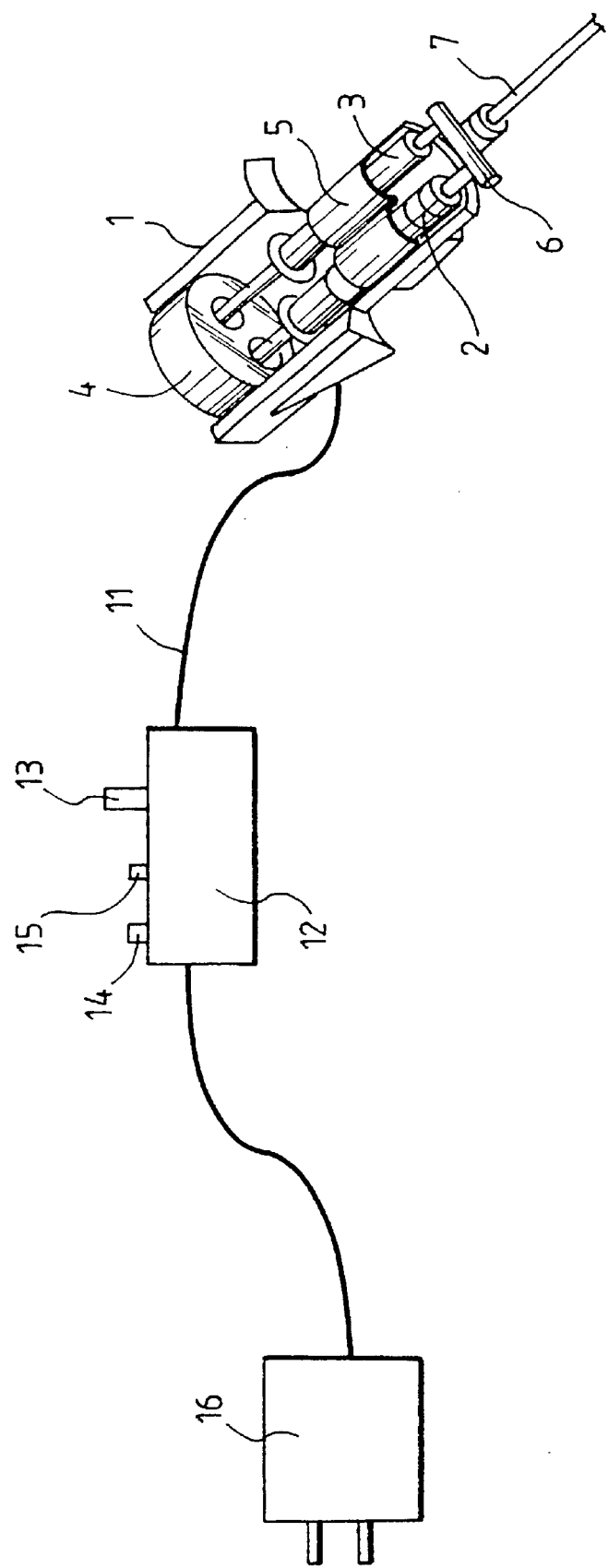
FIG. 1 is a schematic view of a device according to the invention.
Figure 2:
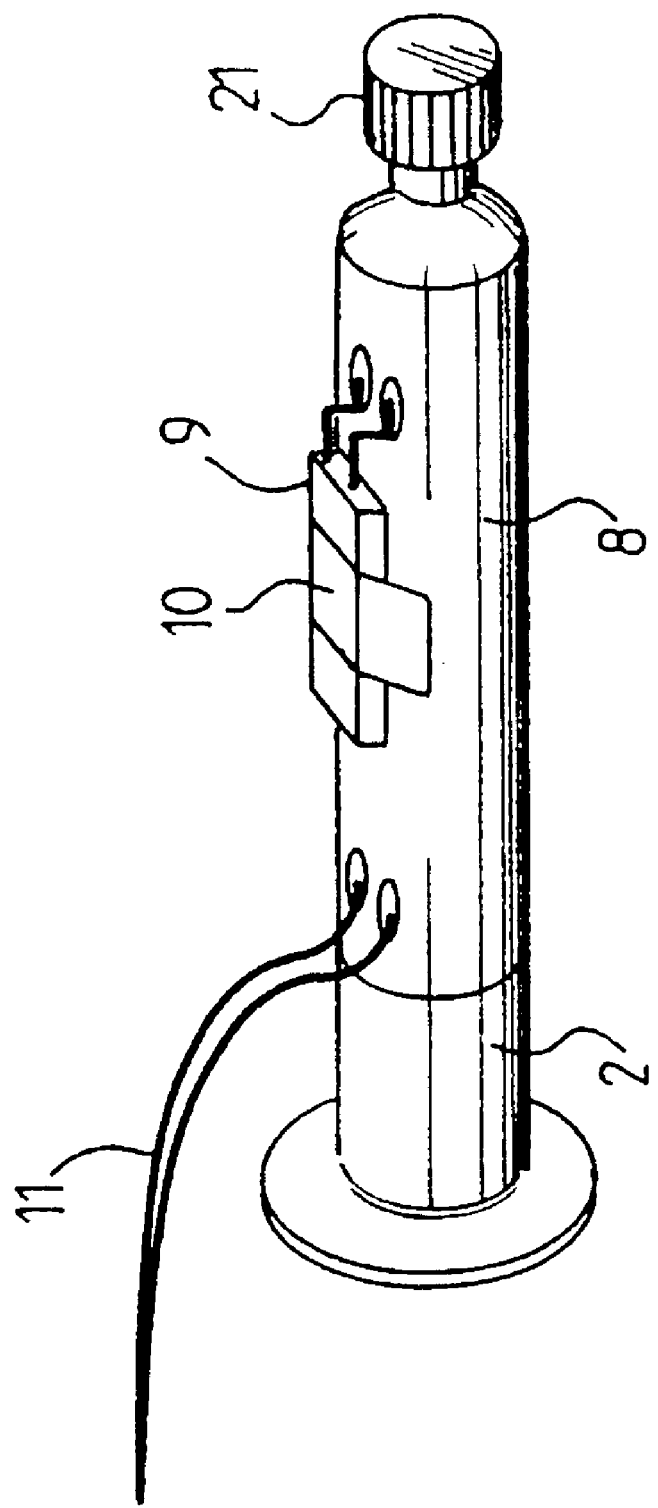
FIG. 2 is a schematic view of a syringe barrel with a thermistor and thermostat.
Figure 3:
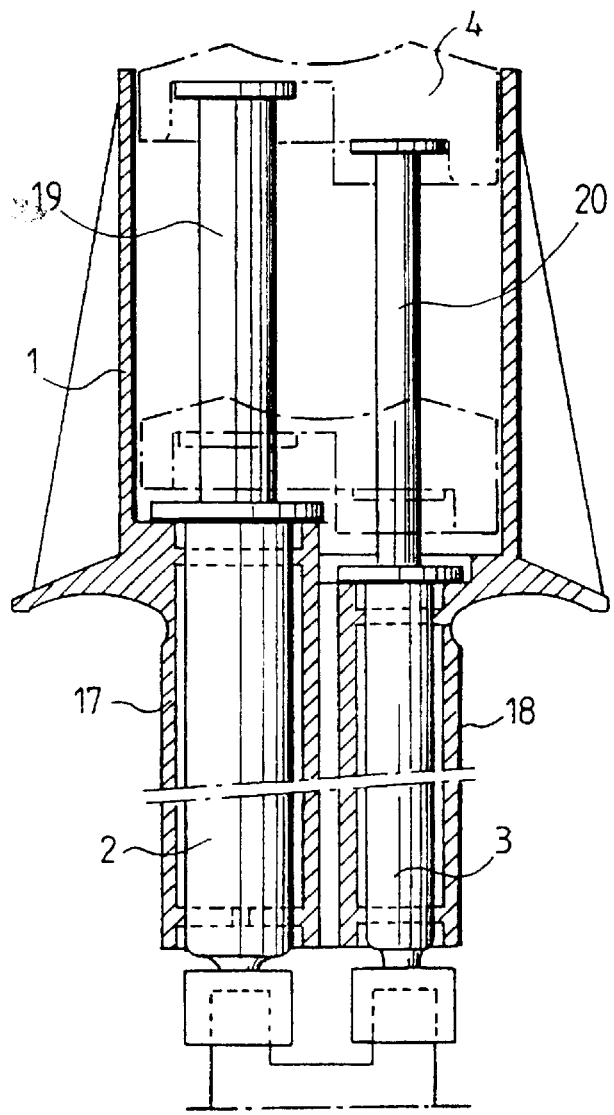
FIG. 3 is a transverse cross-section of the device's receptacle, seen from the front.
Figure 4:
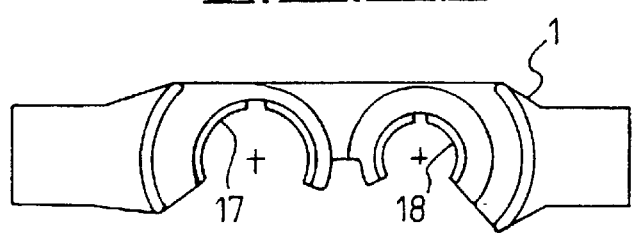
FIG. 4 is a view of this receptacle from above.
Figure 5:
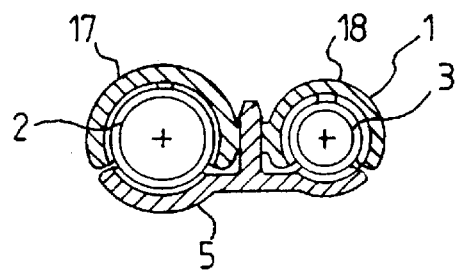
FIG. 5 is a transverse cross-section of this receptacle at the barrel of the syringe.
Figure 6:
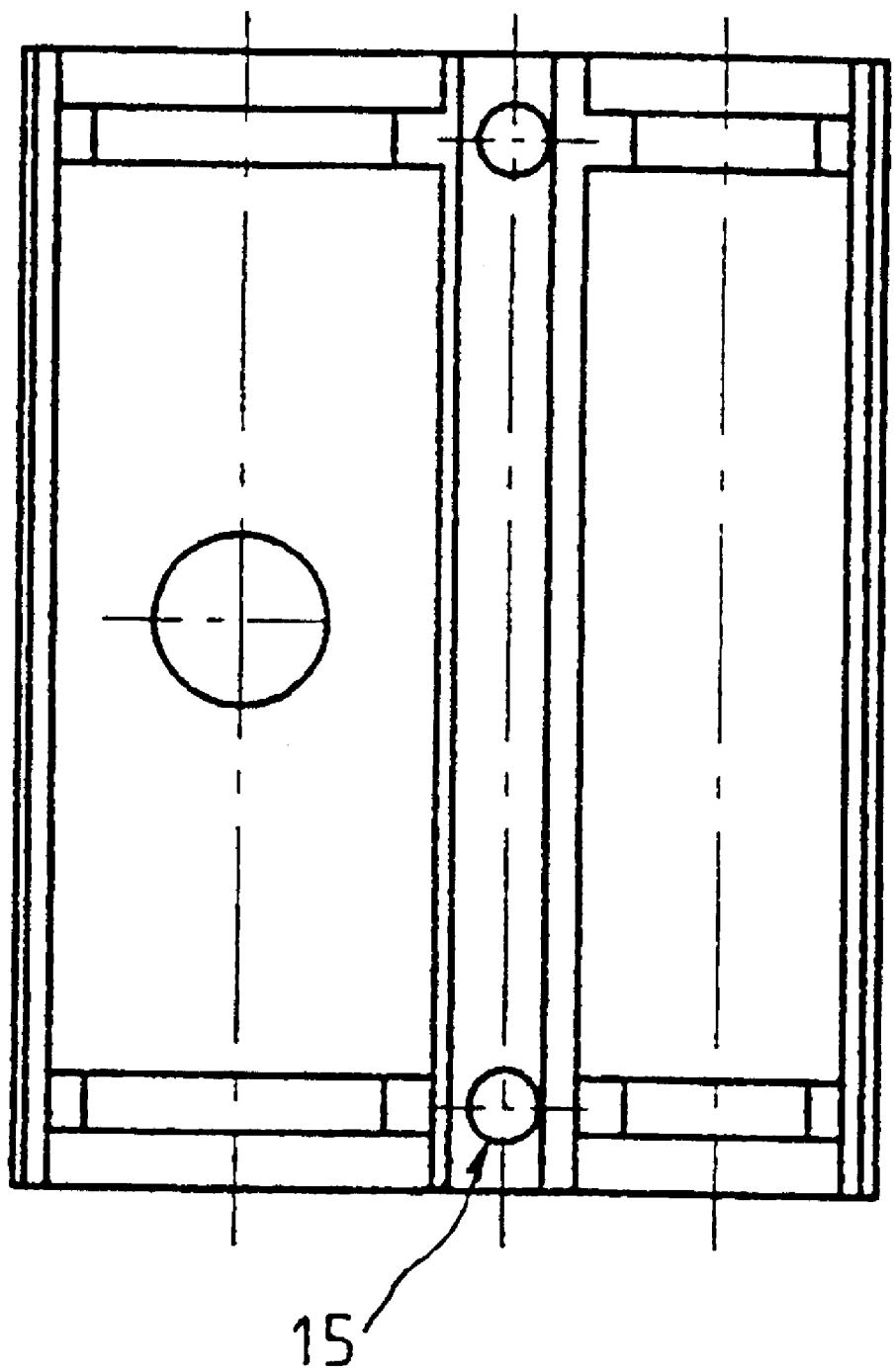
FIG. 6 is an enlarged view of a complementary part of this receptacle used for thermal insulation.

Referring to FIGS. 1 and 2, it can be seen that the device according to the invention includes a receptacle, 1, fitted with two parallel housings suitable for holding two syringe barrels, 2 and 3, of different diameters, the device including a plunger driver, 4, used to expel the contents of the two syringes simultaneously. An extra part, 5, in the form of a double cradle, is used to thermally insulate the two syringe barrels in their respective housings. The outlets of the two syringes are fitted with a connector, 6, which is followed by an extended mixer body or end-piece, 7.

The barrel of the first syringe, 2, which contains the constituent of collagenic origin to be heated, is enclosed in a plastic film, 8, glued to the barrel, 2, and containing a resistance (not visible). This resistance is supplied with electric power by a thermostat, 9, glued onto the film, 8, using metal adhesive, 10, and set to a predetermined temperature, for example, 48° C. This thermostat, 9, controls the electrical power which is carried by two conductors, 11, which lead to an interface box, 12, fitted with a switch, 13, a power indicator light, 14, and a predetermined temperature setting indicator light, 15, which comes on when the thermostat has reached the predetermined temperature setting and maintains this temperature.

The box, 12, is connected by suitable conductors to a power adapter transformer which can be connected to the mains.

Referring to FIGS. 3 to 6, it can be seen that the receptacle, or box, 1, which is fitted with finger-holds to facilitate handling and use by the surgeon, is fitted with two housings in the form of open cylinders, 17, 18, of different diameters, adapted to the diameters of the two syringes, 2 and 3, the internal cross-sections of which are at a fixed ratio which can be chosen between 3 to 1 and 10 to 1 depending on the characteristics of the adhesive mixture to be prepared, for example in a ratio of 4 to 1. The barrels of the syringes are held in the housings by clips, in box 1. The barrels of the syringes are thus immobilized.

Naturally, housing 17 is designed so that it can also house the thermostat, 9, and allow for passage of the conductors, 11, carrying power to the resistance.

The plunger driver, 4, is designed so that it can simultaneously drive the two plunger rods 19, 20 of the two syringes, 2, 3 to ensure simultaneous expulsion of the contents of both syringe barrels, the throughput from syringe 2 naturally being three to ten times greater, for example, four times greater, than the throughput from syringe 3. The conformation of receptacle 1 and the plunger drivers, 4, is such that the surgeon can expel the desired quantity using the fingers of one hand only.

When storing the syringes, their ends are fitted with a cap, 21, to maintain sterile conditions.

The invention is particularly applicable to the adhesives defined in application WO 98/15299, the content of which is included here for reference.

The invention is also applicable to other products for which heating to 37° C. or more is necessary or preferable, such as adhesives or viscoelastic solutions containing highly concentrated macromolecular solutions, the high viscosity of which is reduced at temperatures of around 37 to 50° C., notably preparations partly or totally consisting of fibrinogen, albumin, gelatine, collagen, hyaluronic acid or polysaccharides.

Figure 7:
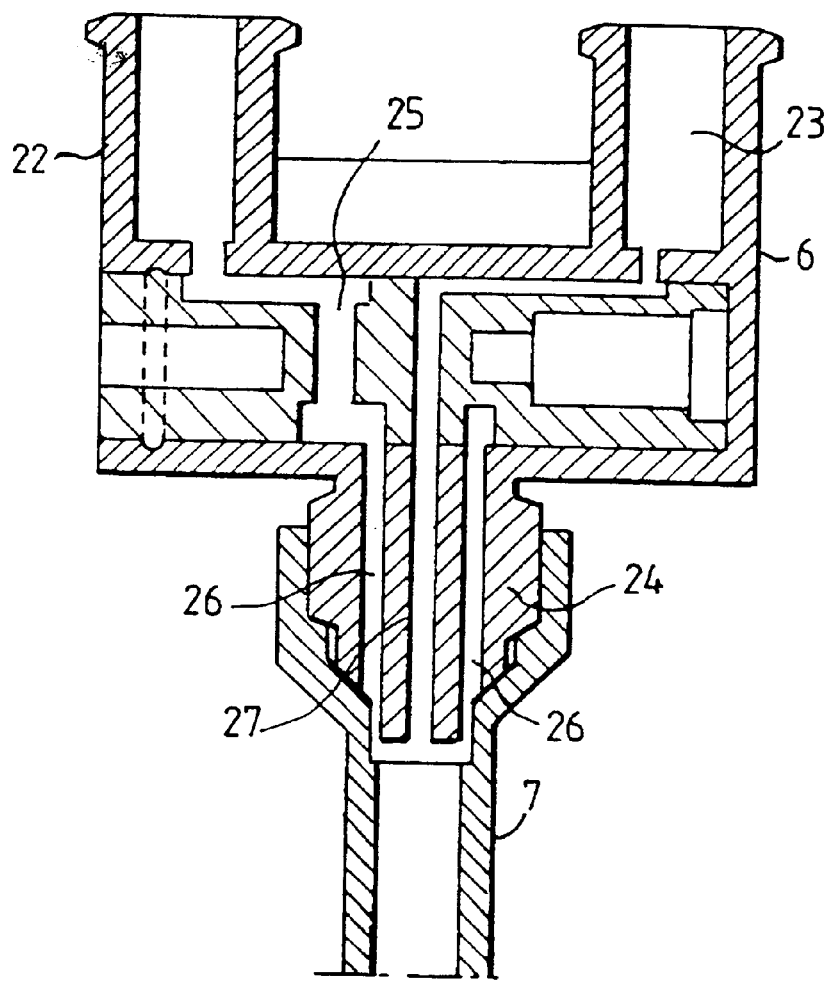
FIG. 7 is a longitudinal cross-section of the connector.
Figure 8:
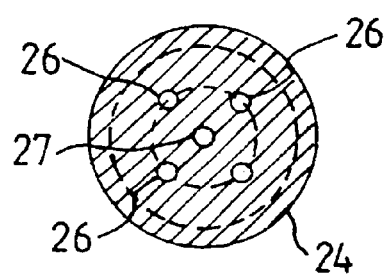
FIG. 8 is a transverse cross-section of this connector taken through the channels.

To assemble the device, remove the caps from the two syringes and slot the connector, 6, which is shown in FIGS. 7 and 8, onto the parallel end-pieces of the two syringes. For this purpose, the connector, 6, is fitted with two tubes, 22, 23 which fit onto the ends of the syringe barrels and, from the other side, a central end-piece, 24, onto which the mixer end-piece, 7, can be slotted. The inside of the tubing, 22, is conical and is continued by a channel, 25, which then splits into four finer channels, 26, distributed equidistantly around the central axis of the end-piece, 24. The conical tubing, 23, is continued by a single channel, 27, which leads into the centre of end-piece 24, channels 26 and 27 having the same diameter.

Figure 9:
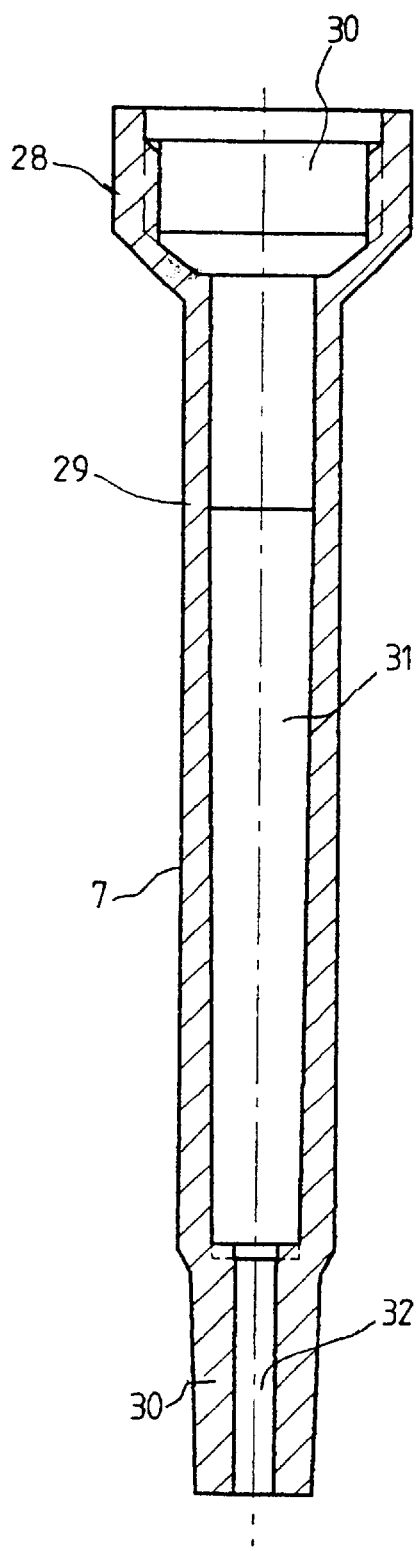
FIG. 9 is a longitudinal cross-section of the mixer end-piece.

The body of the actual mixer, which forms the extended end-piece, 7, is shown in FIG. 9. It has an enlarged proximal extremity, 28, followed by a long cylindrical part, 29, ending at a smaller distal extremity, 30. The central volume of extremity 28 is designed to take end-piece 24 of the connector and continues with a large diameter central channel, 31, which at its other end continues into a channel of smaller cross-section, 32, leading to the outlet of extremity 30.

Figure 12:
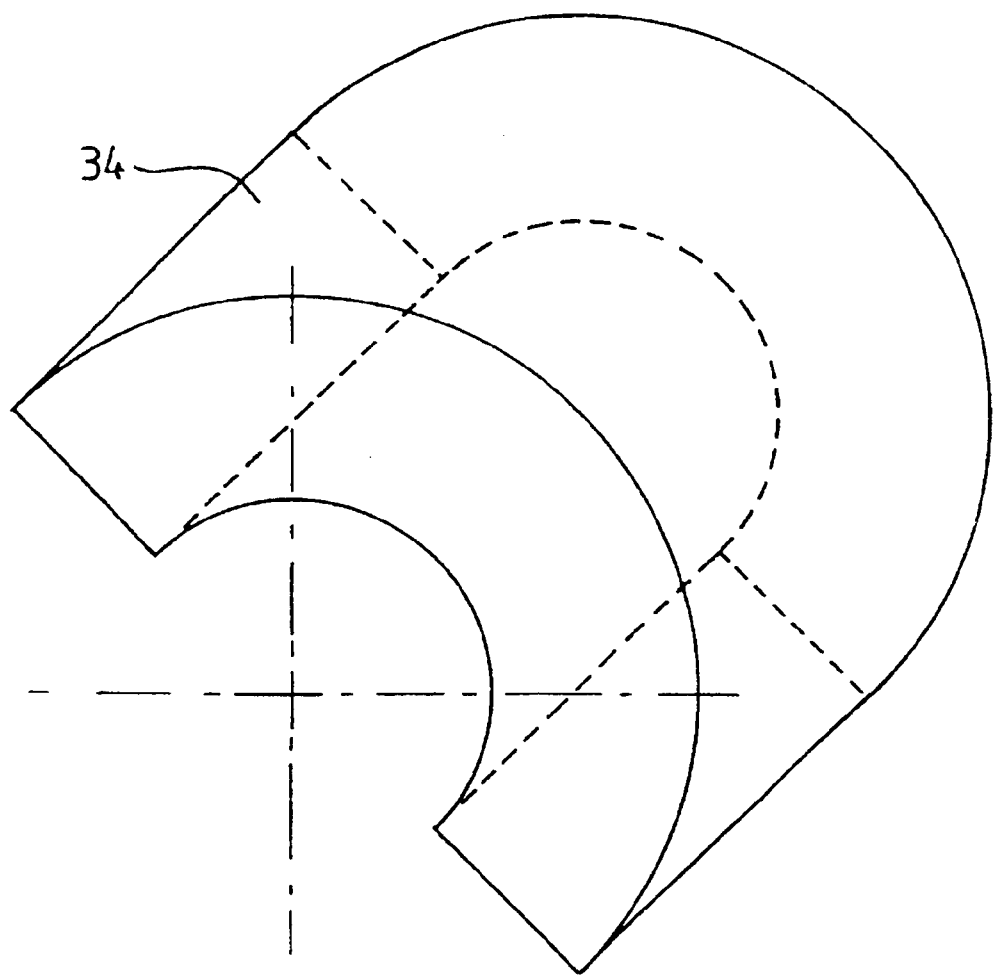
FIG. 12 is a highly enlarged scale view of a particle destined to be contained in the mixer.

Most of channel 31 is filled with particles designed to form a great many baffles to ensure a homogeneous mixture. For example, one of these particles is shown enlarged in FIG. 12 and can be seen to consist of a section of fine plastic tubing cut in two across its diameter. The preferred dimensions of such a particle are as follows:

length: 0.8 mm, external radius: 0.8 mm, internal radius: 0.4 mm.

Figure 11:
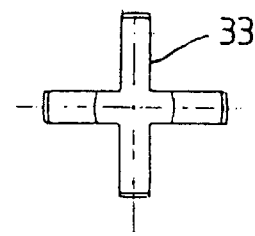
FIG. 11 is a view of this cross-piece from above.
Figure 10:
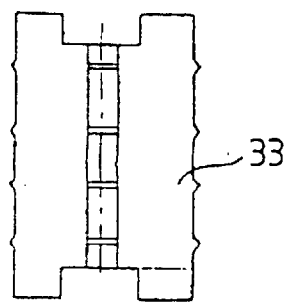
FIG. 10 is an enlarged scale view of a cross-piece which provides internal support for the end-piece.

The intermingled particles form a mass which is retained inside channel 31 by a stopper formed by an extended cross-piece, 33, shown in FIGS. 10 and 11, the arms of which are fitted with small ribs, the cross-piece, 33, being forcibly inserted into the stopper, 7, above the intermingled particles, the dimensions of the cross-piece being such that it does not impede the flow of constituents from the barrels of the syringes but holds the particles, 34, in place.

EXAMPLE 1

The device is used as follows: during preparation of an operation involving the application of surgical adhesive, conductor 11 is connected to interface box 12 and heating is started. When the heating light comes on, the device is ready to use. The surgeon can then expel the desired quantity of mixture by pushing plunger driver 4. The collagenic and polyaldehyde constituents are expelled in a proportional volume of about 4 to 1, for a homogeneous collagen solution, and passing through channels 26 and 27 separately, they enter the central channel, 31, where they come into contact with the intermingled particles, 34. The gradual homogenization of the two constituents forming the mixture lowers the temperature of the collagenic constituent as it comes into contact with the unheated polyaldehyde constituent. The route followed by these constituents and the resulting mixture into end-piece 7, completes lowering of the temperature, so that the homogenized mixture leaves channel 32 at a temperature very close to body temperature, 37° C.

In one variant, the use of the electric syringe includes a prior phase producing a liquid foam of collagen or any other protein used to prepare the adhesive mixture.

EXAMPLE 2

Electric syringe 2 contains a volume of sterile protein solution which is half the maximum volume. It is gradually heated by the electrical resistance to the desired temperature. This syringe 2 is then connected by a simple end-to-end connection with a syringe containing the same volume of air.

Successively pushing and pulling the plungers of the two syringes mixes the respective contents of the two syringes homogeneously. After about 10 push-pull cycles, the foam is retained in syringe 2 where it occupies the maximum volume. This is disconnected. Syringe 2 is then placed in receptacle 1 and the process of producing the adhesive mixture is completed as in the previous example. In this case, the preheated protein constituent and the crosslinking agent are expelled in a proportional volume of about 8 to 1, increased to take into account the volume of air in the foam.

EXAMPLE 3

Syringe 2 contains a volume of sterile water which is half the maximum volume. It is gradually heated by the electrical resistance to the desired temperature. This syringe containing water is then connected, by a simple end-to-end connector, to a syringe containing the necessary quantity of protein in the form of sterile powder with a neutral pH and a quantity of air, the total volume of which is the same as that of the electric syringe full of water.

The contents of the 2 syringes are mixed by successively pushing and pulling the plungers of both syringes to prepare a homogeneous liquid protein foam, and after placing syringe 2 in receptacle 1, the mixture is used as in example 2.

EXAMPLE 4

The heating syringe, 2, contains a volume of sterile protein solution which is half the maximum volume, to which is added the same volume of sterile air.

The biphasic content of this syringe is gradually heated by the electrical resistance to the desired temperature. The electric syringe is then connected by a simple end-to-end connector, to an empty sterile syringe with an initial volume of zero but adequate potential volume.

The protein foam can be prepared and homogenized in syringe 2 by successively pushing and pulling the plungers of the two syringes.

After about 10 push-pull cycles, the protein foam is maintained at the required temperature in the electric syringe of which it occupies the maximum volume. The empty syringe is disconnected. Then, the process to prepare the final adhesive mixture is performed as described above. In this case, the preheated protein constituent and the crosslinking agent are expelled in a proportional volume of about 8 to 1, increased to take into account the volume of air in the foam.

EXAMPLE 5

Syringe 2 contains a volume of sterile water which is half the maximum volume, with the same volume of sterile air added to it. The biphasic content of this syringe is gradually heated by the electrical resistance to the desired temperature. The electric syringe is then connected by a simple end-to-end connector, to a syringe of adequate potential volume, containing the necessary quantity of protein in the form of sterile dry powder with a neutral pH.

The contents of the two syringes are mixed by successively pushing and pulling the plungers of both syringes to prepare a homogeneous liquid protein foam and the mixture is then used as in the previous example.

EXAMPLE 6

Syringe 2 contains the necessary quantity of protein in the form of a dry, sterile powder, with a neutral pH, to which a volume of air equal to half the maximum volume of the syringe has been added.

The electric syringe is immediately connected by a simple end-to-end connector to a second sterile syringe containing a quantity of sterile of water equal to half the volume of the electric syringe.

The sterile water is injected into the electric syringe where it gradually wets the dry powder.

The content of this syringe is then gradually heated to the desired temperature by the electrical resistance. Successively pushing and pulling on the plungers of the two syringes prepares and homogenizes the protein foam in syringe 2. After about 10 push-pull cycles, the foam is maintained at the required temperature in the electric syringe. The empty syringe is disconnected. Then, the process of preparing the final adhesive mixture is performed as in the previous examples.

EXAMPLE 7

The device, 1, with two parallel syringes, 2 and 3, of the present invention is fitted with a third syringe full of air, which is connected via a special additional tube, to the mixer, 7, inlet, so that the air is automatically incorporated into the adhesive mixture during preparation, from the moment when the operator pushes the contents of the three sterile syringes, simultaneously, using a special support such as a receptacle with three syringe housings and an appropriate driver.

What is claimed is:

1. A device for the formation and delivery of a mixture to a person, comprising:

a receptacle adapted to the shape of an operator's hand and including a holder which holds a first and second barrel of two syringes, respectively, a first one of the two syringes containing a first constituent of the mixture and a second one of the two syringes containing a second constituent of the mixture;

an expelling device which can simultaneously expel the first constituent and second constituent of the first syringe and second syringe, respectively;

a heater which maintains the constituent in the first syringe at a predetermined temperature setting which is higher than body temperature; and a mixer which simultaneously receives the first constituent and second constituent of the first syringe and second syringe during application, and the mixer provides cooling.

2. The device as in claim 1, wherein the heater includes an electrical resistance or thermistor.

3. The device as in claim 2, wherein the electrical resistance or thermistor is permanently fastened to the barrel of the first syringe containing the first constituent of the mixture.

4. The device as in claim 3, wherein the resistance or thermistor is fastened to a film surrounding the barrel of the first syringe.

5. The device as in claim 1, further comprising a first thermostat controlling electrical power of the heater and detecting that the first constituent has reached the predetermined temperature setting to maintain the predetermined temperature, and to send out a signal indicating that the predetermined temperature setting has been reached.

6. The device as in claim 5, wherein the first thermostat is fastened to the barrel of the first syringe containing the first constituent.

7. The device as in claim 5, further comprising a second backup thermostat, set to cut off a power supply to the thermistor or electrical resistance, when a safety temperature threshold, higher than the predetermined temperature setting, is reached or exceeded, and not to allow the power supply to be reconnected until the temperature has fallen below the predetermined temperature setting.

8. The device as in claim 1, wherein the mixer comprises an extended mixer body having two extremities, the extended mixer body simultaneously receiving the first constituent and the second constituent through one of the two extremities when the operator expels the first constituent and second constituent from the two syringes.

9. The device as in claim 8, wherein the extended mixer body is fitted with a channel filled with intermingled particles.

10. The device as in claim 9, wherein the intermingled particles are formed of sections of tubing cut across the diameter of the tubing.

11. The device as in claim 10 wherein the sections of tubing have roughly the following dimensions: length: 0.8 mm, external radius: 0.8 mm, internal radius: 0.4 mm.

12. The device as in claim 9, wherein the particles are retained inside the channel by a cross-piece pushed in by force.

13. The device as in claim 9, wherein the length of the extended mixer body or end-piece of the mixer is between 2 and 4 cm.

14. The device as in claim 1, wherein the mixer is fitted with a connector which can be fastened to ends of the barrels of the two syringes via two conical tubes, respectively, and the mixer includes an extended mixer body which can be fitted to one end of the connector.

15. The device as in claim 14, wherein the connector has a central channel which communicates with the barrel of the second syringe and several equidistant channels which are in communication with the barrel of the first syringe.

16. The device as in claim 1, wherein the receptacle is fitted with two housings suitable for holding the barrels of the two syringes, respectively, and an extra part which has complementary cradle shapes for thermal insulation of the barrels of the two syringes in the two housings, and the extra part is linked to a plunger driver which enables a first and a second plunger rod of the two syringes to be operated simultaneously.

17. The device as in claim 1, wherein the ratio of cross-sections, and hence volumes, of the barrels of the two syringes is 3 to 10 for a liquid mixture and from 6 to 10 for a foam mixture.

18. The device as in claim 17, wherein to prepare a liquid mixture, the ratio is of the order of 4.

19. The device as in claim 1, wherein the first constituent comprises a substance of collagenic origin and the second constituent comprises a crosslinking agent.

20. The device as in claim 19, wherein the substance of collagenic origin is a solution of collagen which has at least partly lost is spiral, non-hydrolyzed structure, consisting mainly of alpha chains.

21. The device as in claim 19, wherein the crosslinking agent is a solution of oxidized starch.

22. The device as in claim 1, wherein the predetermined temperature setting at which the first constituent is maintained, is between 42° C. and 57° C.

23. The device as in claim 22, wherein the predetermined temperature setting at which the first constituent is maintained, is between 44° C. and 50° C. for direct application on expulsion from the mixer.

24. The device as in claim 22, wherein the predetermined temperature setting at which the first constituent is maintained is between 48° C. and 54° C. for application via a tube.

25. A syringe suitable for use in the device of claim 1 and including the heater which maintains contents of the syringe at a predetermined temperature setting which is higher than body temperature.

26. The syringe of claim 25, wherein the heater includes an electrical resistance or thermistor.

27. A process for the production of a mixture destined to be formed and delivered by using the device of claim 1, comprising:

mixing a first constituent of the mixture in the barrel of the first syringe, or inserting the first constituent into the barrel of the first syringe.

28. The process of claim 27, further comprising:

introducing a gas into the mixer at the same time as the first and second constituents are mixed to produce a mixture in the form of a foam.

29. The process of claim 27, further comprising:

introducing a first constituent in the form of a foam containing the components of the first constituent and a gas into the first syringe fitted with the heater which can maintain the temperature of the syringe to produce a mixture in the form of a foam, or forming a mixture in the form of a foam comprising the first constituent in the first syringe.

30. The process of claim 29, further comprising:

connecting a third syringe to the barrel of the first syringe, fitted with the heater, distributing the components of the first constituent, selected from the group consisting of:
   (a) a liquid phase and a gas, or
   (b) a liquid phase, a solid pulverulent and a gas,
in either the first syringe or the third syringe, to produce the foam or, distributing components of the first constituent between the first syringe and the third syringe to produce the foam by successive transfers from the first syringe to the third syringe.

31. The device of claim 1, wherein the second syringe containing the second constituent is kept at room temperature.

* * * * *